(12) United States Patent
Hallisey et al.

(10) Patent No.: US 11,413,049 B2
(45) Date of Patent: Aug. 16, 2022

(54) MICROCATHETER OCCLUSION EMBOLIZATION CATHETER

(71) Applicant: Merit Medical Systems, Inc., South Jordan, UT (US)

(72) Inventors: Michael Hallisey, Wethersfield, CT (US); Tony Vincent Jacques, Bristol, CT (US); Jeffrey P. Radziunas, Wallingford, CT (US)

(73) Assignee: Merit Medical Systems, Inc., South Jordan, UT (US)

( * ) Notice: Subject to any disclaimer, the term of this patent is extended or adjusted under 35 U.S.C. 154(b) by 394 days.

(21) Appl. No.: 16/366,354

(22) Filed: Mar. 27, 2019

(65) Prior Publication Data

US 2019/0298389 A1    Oct. 3, 2019

Related U.S. Application Data

(60) Provisional application No. 62/717,345, filed on Aug. 10, 2018, provisional application No. 62/761,512, filed on Mar. 28, 2018.

(51) Int. Cl.
| | | |
|---|---|---|
| *A61B 17/12* | (2006.01) | |
| *A61M 25/00* | (2006.01) | |
| *A61M 25/09* | (2006.01) | |
| *A61B 17/00* | (2006.01) | |

(52) U.S. Cl.
CPC .. *A61B 17/12186* (2013.01); *A61B 17/12109* (2013.01); *A61B 17/12136* (2013.01);
(Continued)

(58) Field of Classification Search
CPC ........ A61B 17/12186; A61B 17/12136; A61B 17/12109; A61B 17/12031; A61B 17/1204; A61B 2017/00893; A61M 25/0075; A61M 25/003; A61M 25/007; A61M 25/10; A61M 2025/0073; A61M 2025/0042;
(Continued)

(56) References Cited

U.S. PATENT DOCUMENTS

| | | | |
|---|---|---|---|
| 5,360,403 A | | 11/1994 | Mische |
| 5,599,307 A | * | 2/1997 | Bacher ...................... A61F 2/82 |
| | | | 604/101.05 |

(Continued)

FOREIGN PATENT DOCUMENTS

| | | |
|---|---|---|
| EP | 2695637 | 2/2014 |
| WO | 199717998 | 5/1997 |

(Continued)

OTHER PUBLICATIONS

International Search Report and Written Opinion dated Jul. 11, 2019 for PCT/US2019/024351.
European Search Report dated Nov. 29, 2021 for EP19777331.0.

*Primary Examiner* — Richard G Louis
*Assistant Examiner* — Chima U Igboko
(74) *Attorney, Agent, or Firm* — Dorsey & Whitney LLP

(57) ABSTRACT

Devices used to deliver a substance within a patient's body are disclosed. The devices may include a microcatheter configured to deliver the substance to a targeted site. The microcatheter may include an expandable member to temporarily restrict blood flow in a vessel, a flow restriction member to restrict flow of material out a distal end of the microcatheter, and a port disposed proximal of the expandable member.

14 Claims, 5 Drawing Sheets

(52) U.S. Cl.
CPC ........ *A61M 25/0075* (2013.01); *A61M 25/09* (2013.01); *A61B 2017/00893* (2013.01); *A61M 2025/0042* (2013.01); *A61M 2025/0073* (2013.01)

(58) Field of Classification Search
CPC .. A61M 2025/0079; A61M 2025/1061; A61M 2025/0025; A61M 2025/1052; A61M 25/09
See application file for complete search history.

(56) References Cited

U.S. PATENT DOCUMENTS

| | | | |
|---|---|---|---|
| 5,645,533 A * | 7/1997 | Blaeser | A61M 25/104 604/164.01 |
| 6,045,531 A * | 4/2000 | Davis | A61M 25/10 604/101.05 |
| 6,638,243 B2 * | 10/2003 | Kupiecki | A61M 25/0075 604/509 |
| 9,782,185 B2 | 10/2017 | Solar et al. | |
| 2005/0059931 A1 * | 3/2005 | Garrison | A61M 25/1011 604/101.04 |
| 2014/0012306 A1 | 1/2014 | Zhadkevich | |
| 2015/0359998 A1 * | 12/2015 | Carmel | A61M 5/14 604/509 |
| 2017/0281915 A1 * | 10/2017 | Jalgaonkar | A61M 25/1011 |

FOREIGN PATENT DOCUMENTS

| | | |
|---|---|---|
| WO | 199904845 | 2/1999 |
| WO | 2004110543 | 12/2004 |
| WO | 2014036530 | 3/2014 |
| WO | 2015189354 | 12/2015 |

* cited by examiner

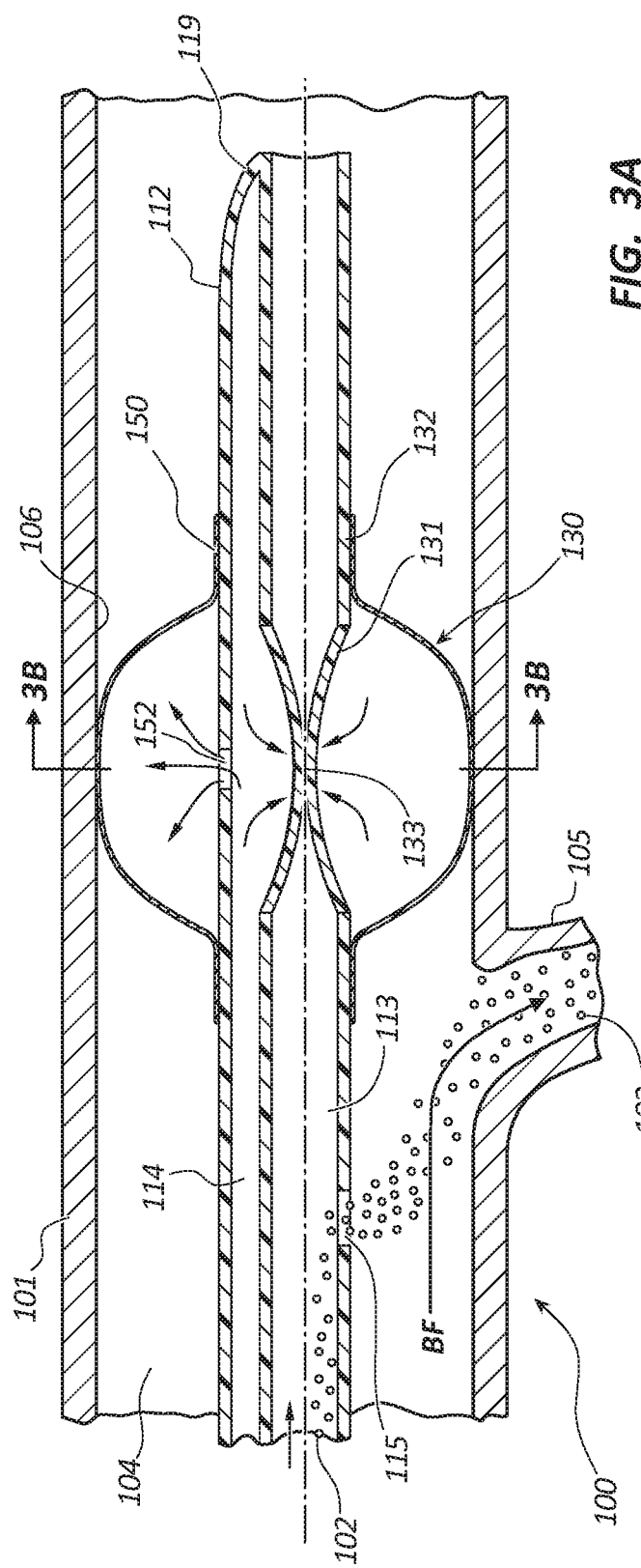
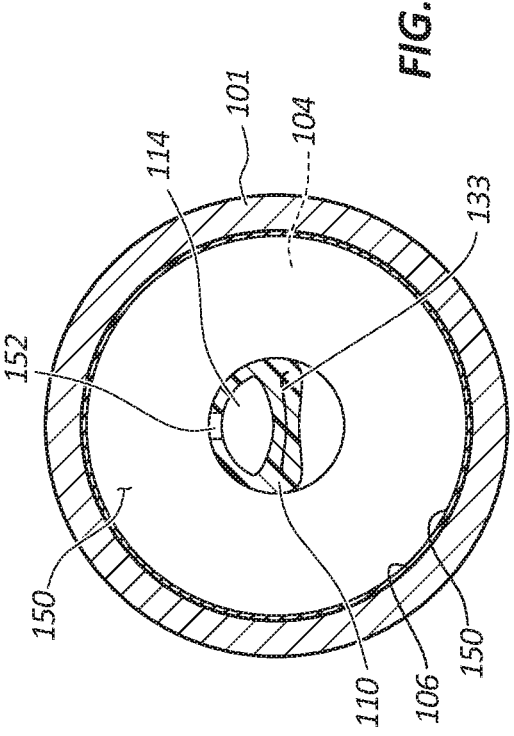
FIG. 3A
FIG. 3B

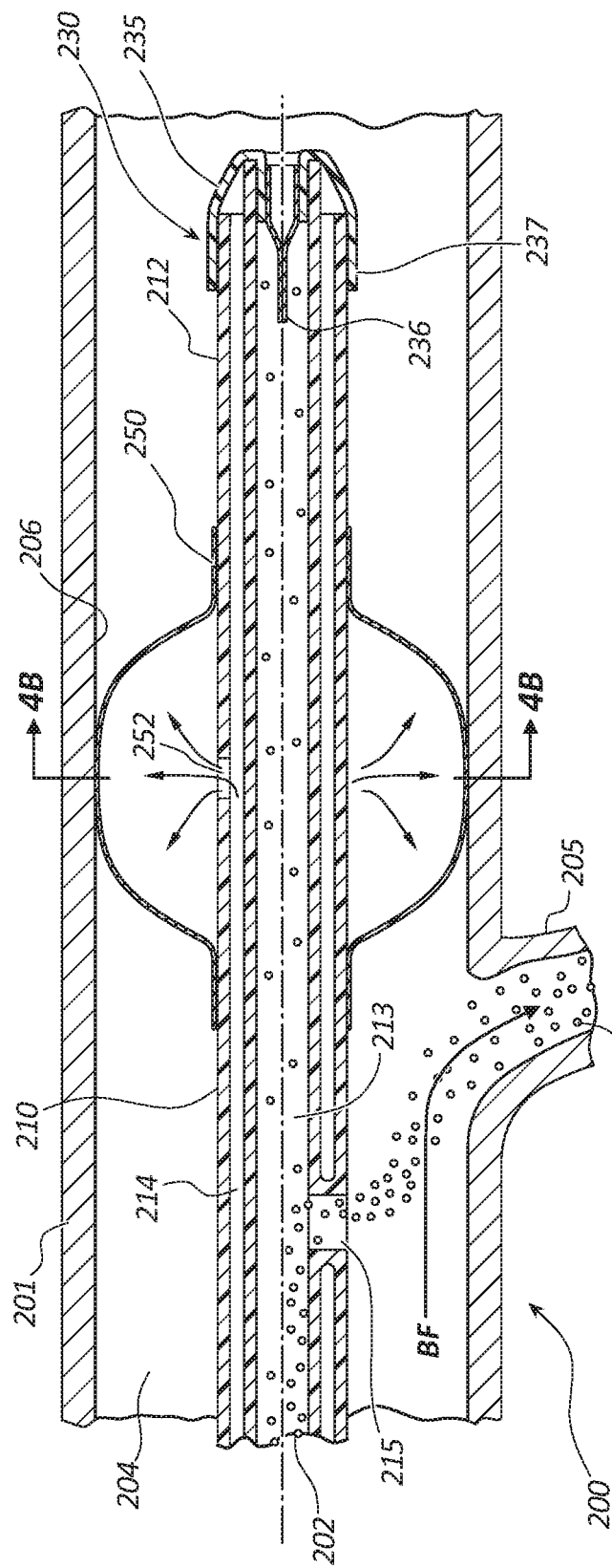
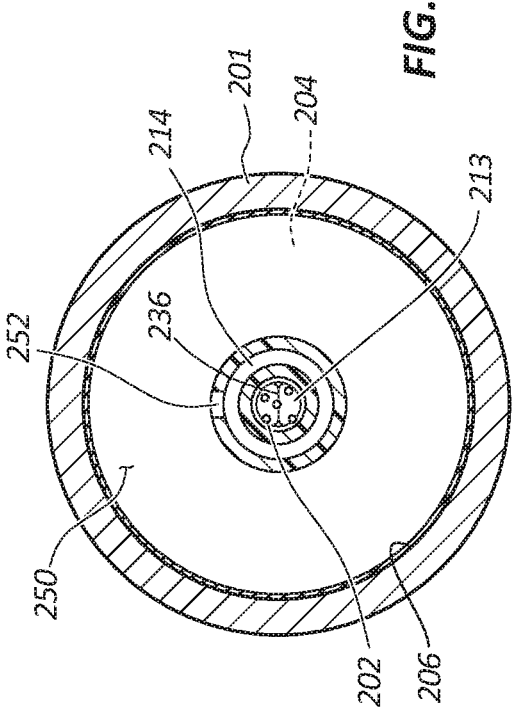
FIG. 4A
FIG. 4B

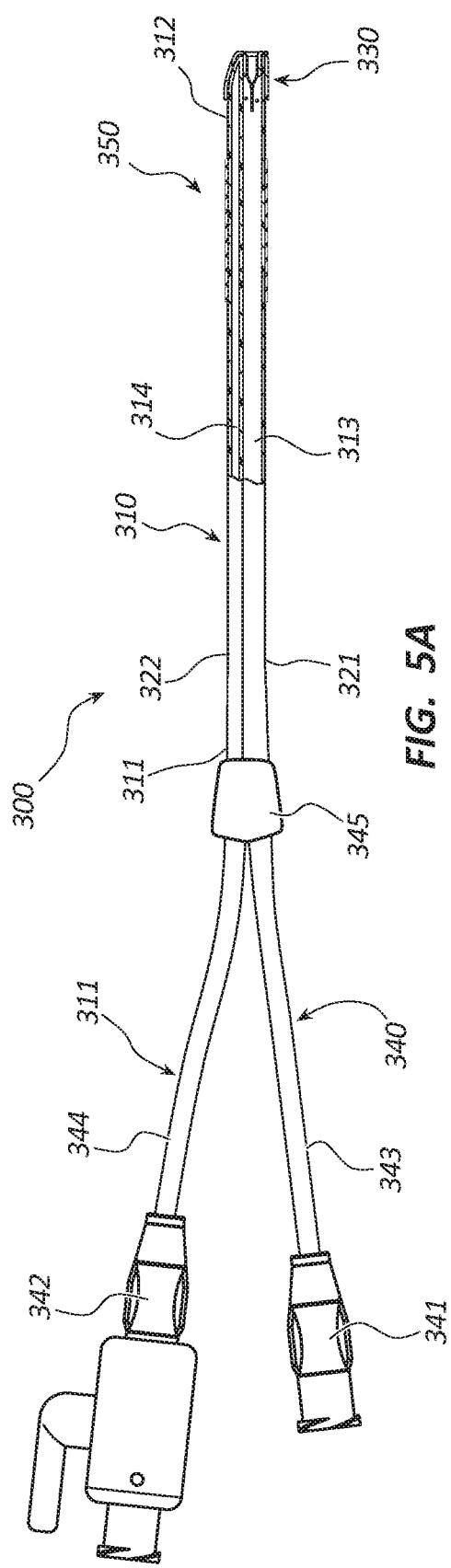
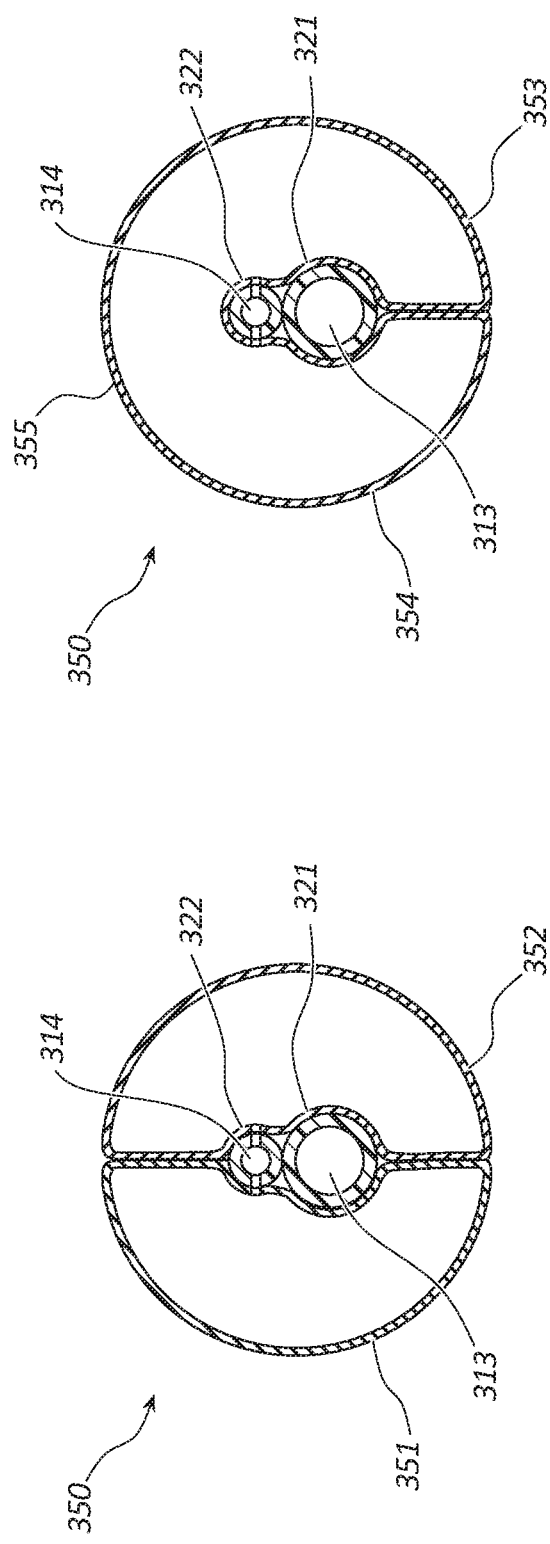
FIG. 5A
FIG. 5B
FIG. 5C

MICROCATHETER OCCLUSION EMBOLIZATION CATHETER

RELATED CASES

This application claims priority to U.S. Provisional Application No. 62/761,512, filed on Mar. 28, 2018 and titled "MICROCATHETER OCCLUSION EMBOLIZATION CATHETER," and to U.S. Provisional Application No. 62/717,345, filed on Aug. 10, 2018 and titled "EMBOLIC BALLOON CATHETER CONCEPTS," both of which are hereby incorporated by reference in their entirety.

TECHNICAL FIELD

The present disclosure relates generally to devices used to deliver a substance within a patient's body. More specifically, the present disclosure relates to a microcatheter device used to temporally occlude a vessel and deliver an embolization material to a targeted site within the vessel to embolize the vessel.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 3A is a side cross-sectional view of a distal portion of the embolization catheter of FIG. 1 in an occlusion state, the embolization catheter disposed within a vessel.

FIG. 3B is a transverse cross-sectional view, taken through plane 3B-3B of FIG. 3A, of a distal portion of the embolization catheter in the occlusion state, the embolization catheter disposed within a vessel.

FIG. 4A is a side cross-sectional view of a distal portion of another embolization catheter in an occlusion state, the embolization catheter disposed within a vessel.

FIG. 4B is a transverse cross-sectional view, taken through plane 4B-4B of FIG. 4A, of a distal portion of the embolization catheter of FIG. 4A in the occlusion state, the embolization catheter disposed within a vessel.

FIG. 5A is a side view of another embolization catheter.

FIG. 5B is a transverse cross-sectional view of a distal portion of the embolization catheter of FIG. 5A in an occlusion state.

FIG. 5C is a transverse cross-sectional view of an alternative embodiment of the embolization catheter of FIG. 5A in the occlusion state.

DETAILED DESCRIPTION

Figure 1:
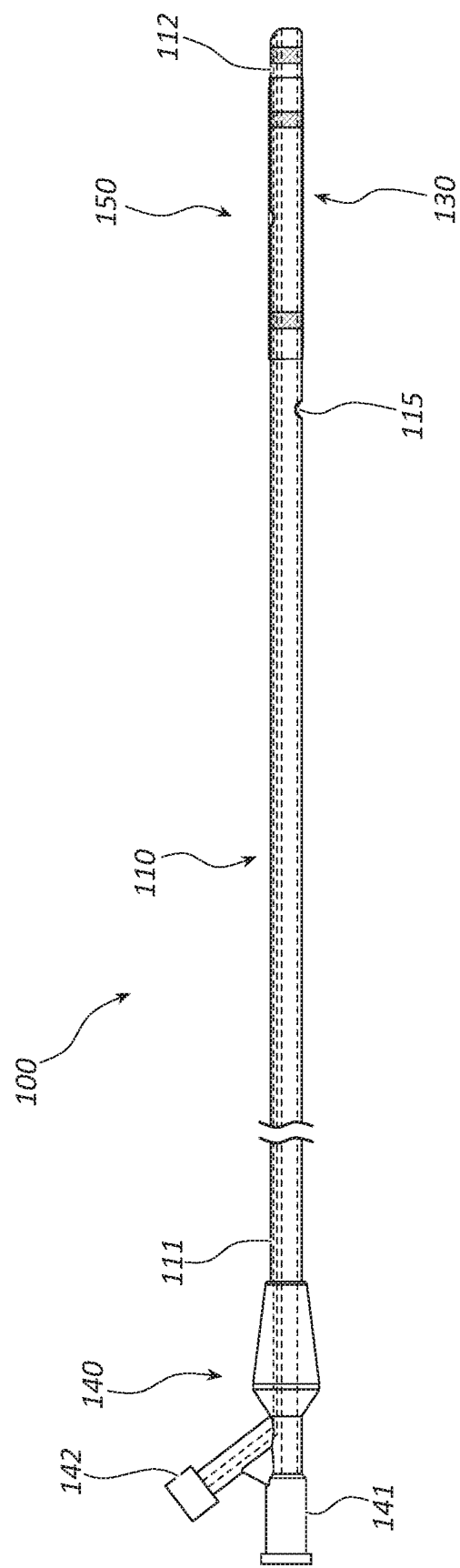
FIG. 1 is a side view of an embodiment of an embolization catheter.

Some tumors or lesions within a human body may be vascularized. Vascularized tumors or lesions include hepatomas, uterine fibroids, arteriovenous malformations, prostatic hyperplasia, etc. In some instances, treatment of the tumors or lesions may be accomplished by a vessel embolization procedure. The embolization procedure may utilize an embolization catheter to deliver an embolic material to a targeted vessel adjacent the tumor or lesion. Once delivered, the embolic material may be configured to occlude the vessel to prevent or limit blood flow to the tumor or lesion. The limiting of blood flow to the tumor or lesion restricts the cells of the tumor or lesion from receiving oxygen and nutrients resulting in death of the cells and shrinkage of the tumor or lesion.

An embolization catheter used in a vessel embolization procedure may include an elongate body comprising two lumens. One lumen may be used to deliver the embolic material into the vessel, and the other lumen may be used to deliver air, saline, or other fluid to an expandable member to expand the expandable member. The expandable member may be a balloon used to occlude the vessel or a portion of the vessel when the balloon is expanded to temporarily restrict blood flow distally of the embolization catheter. In some instances, the embolization catheter may also include a port in fluid communication with the lumen used to deliver the embolic material. The port may be positioned proximal of the expandable member such that the embolic material may be delivered into the vessel proximal of the occlusion by the expandable member. Certain embolization catheters within the scope of this disclosure include a valve member disposed distal of the port. The valve member may be configured to direct flow of the embolic material through the port and prevent the embolic material from flowing out the end of the embolization catheter.

Embodiments may be understood by reference to the drawings, wherein like parts are designated by like numerals throughout. It will be readily understood by one of ordinary skill in the art, having the benefit of this disclosure, that the components of the embodiments, as generally described and illustrated in the figures herein, could be arranged and designed in a wide variety of different configurations. Thus, the following more detailed description of various embodiments, as represented in the figures, is not intended to limit the scope of the disclosure, but is merely representative of various embodiments. While the various aspects of the embodiments are presented in drawings, the drawings are not necessarily drawn to scale unless specifically indicated.

Various features are sometimes grouped together in a single embodiment, figure, or description thereof for the purpose of streamlining the disclosure. Many of these features may be used alone and/or in combination with one another.

The phrases "coupled to" and "in communication with" refer to any form of interaction between two or more entities, including mechanical, electrical, magnetic, electromagnetic, fluid, and thermal interaction. Two components may be coupled to or in communication with each other even though they are not in direct contact with each other. For example, two components may be coupled to or in communication with each other through an intermediate component.

The directional terms "distal" and "proximal" are given their ordinary meaning in the art. That is, the distal end of a medical device means the end of the device furthest from the practitioner during use. The proximal end refers to the opposite end, or the end nearest the practitioner during use. As specifically applied to an embolization catheter, the proximal end of the embolization catheter refers to the end outside the patient's body and the distal end refers to the opposite end, the end inserted into the patient's body or the end away from the physician. Even if at one or more points in a procedure a physician changes the orientation of the embolization catheter, as used herein, the term "proximal end" always refers to the end not configured for insertion into the patient, such as a hub end, even if the distal end is temporarily closer to the physician.

"Fluid" is used in its broadest sense, to refer to any fluid, including both liquids and gases as well as solutions, compounds, suspensions, etc., which generally behave as fluids.

FIGS. 1-5C illustrate different views of several embolization catheters and related components. In certain views each device may be coupled to, or shown with, additional components not included in every view. Further, in some views only selected components are illustrated, to provide detail into the relationship of the components. Some components may be shown in multiple views, but not discussed in connection with every view. Disclosure provided in connection with any figure is relevant and applicable to disclosure provided in connection with any other figure or embodiment.

FIGS. 1-3B depict an embodiment of an embolization catheter 100. In the illustrated embodiment, the embolization catheter 100 comprises a body 110, an expandable member 150, a flow restriction or valve member 130, and a hub or handle portion 140. The body 110 may comprise a tubular structure extending from a proximal end 111 to a distal end 112. The distal end 112 may comprise a tip 119. The tip 119 may be configured to be atraumatic such that it does not damage a vessel wall 106 when the body 110 is advanced through a vessel 101. The body 110 may be formed of any suitable biocompatible and hemocompatible material. For example, the body 110 may be formed of stainless steel, nitinol, polyurethane, nylon, poly ether amide copolymer, etc. In some embodiments, the length of the body 110 may range from about 20 cm to about 300 cm, from about 50 cm to about 200 cm, and from about 80 cm to about 150 cm. Further, the diameter of the body 110 may range from about 1.2 French to about 3.8 French, or may range from 1 French to 5 French, or other ranges. In some embodiments, the diameter of the body 110 is consistent from the proximal end 111 to the distal end 112. In other embodiments, the diameter of the body 110 is larger at the proximal end 111 than at the distal end 112, such as embodiments wherein the body 110 is tapered along its longitudinal length or along any portion of its longitudinal length. In certain embodiments, the body 110 comprises a distal tip 119 that is tapered and may be more flexible than the remainder of the body 110. In some instances, the body 110 is constructed with a braid or coil configured to increase structural characteristics, such as burst strength, pushability, torque transfer, etc. The braid or coil may be formed from any suitable material, such as stainless steel, platinum, carbon, tungsten, nitinol, etc. Further, the body 110 may comprise a lubricious coating, such as a hydrophilic coating. Additionally or alternatively, the body 110 comprises one or more radiopaque markers or bands disposed adjacent the distal end 112.

In the embodiment of FIGS. 1-3B, the body 110 includes two lumens, an embolic material delivery or guidewire lumen 113 and a pressurization lumen 114. In other embodiments, the body 110 may include three, four, five, or more lumens. In the illustrated embodiment, the lumens 113, 114 extend in parallel from the proximal end 111 to the distal end 112. In other embodiments, the guidewire lumen 113 may be coaxially disposed within the pressurization lumen 114. The guidewire lumen 113 may be sized to accommodate a guidewire, including guidewires with diameters ranging from about, 0.25 mm to about 0.75 mm, including from about 0.406 mm to about 0.635 mm. In some embodiments, the guidewire lumen 113 includes a lubricious liner, such as a polytetrafluoroethylene liner. The pressurization lumen 114 may be sized to allow passage of air or fluid to expand the expandable member 150.

The body 110 may comprise a proximal port 115. In the illustrated embodiment, the proximal port 115 is disposed proximal of the expandable member 150 and is in fluid communication with the guidewire lumen 113. The proximal port 115 may be configured to permit flow of fluid and/or embolic material from the guidewire lumen 113, through the proximal port 115, and into a vessel lumen 104. The proximal port 115 may be formed such that an inner diameter is smaller than an outer diameter. In other words, the proximal port 115 may be skived or cut into an outer wall of the body 110 such that the proximal port 115 is funnel shaped or flared toward the outside. The inner diameter of the proximal port 115 may be sized to accommodate passage of embolic material 102 through the proximal port 115. The particle size of the embolic material 102 may range from about 20 μm to about 400 μm, from about 50 μm to about 350 μm, or from about 100 μm to about 300 μm.

As shown in the illustrated embodiment, the expandable member 150 may be disposed adjacent the distal end 112 of the body 110. The expandable member 150 may circumferentially surround the body 110. In the illustrated embodiment, the expandable member 150 is fixedly coupled to the body 110 at a proximal end and a distal end of the expandable member 150. An internal volume of the expandable member 150 is in fluid communication with the pressurization lumen 114 through a pressurization port 152. In some embodiments, the expandable member 150 may be a balloon. The expandable member 150 may be formed from any suitable elastomeric material. For example, the expandable member 150 may be formed from a thermoplastic elastomer, silicone rubber, latex rubber, natural rubber, etc. In another embodiment, the expandable member 150 may be formed from a semi-compliant or non-compliant material, such as polyurethane, nylon, poly ether amide copolymer, etc. The length of the expandable member 150 may range from about 5 mm to about 30 mm, range from about 10 mm to about 20 mm, or be about 15 mm. An expanded diameter of the expandable member 150 may be about 3 mm.

Figure 2A:
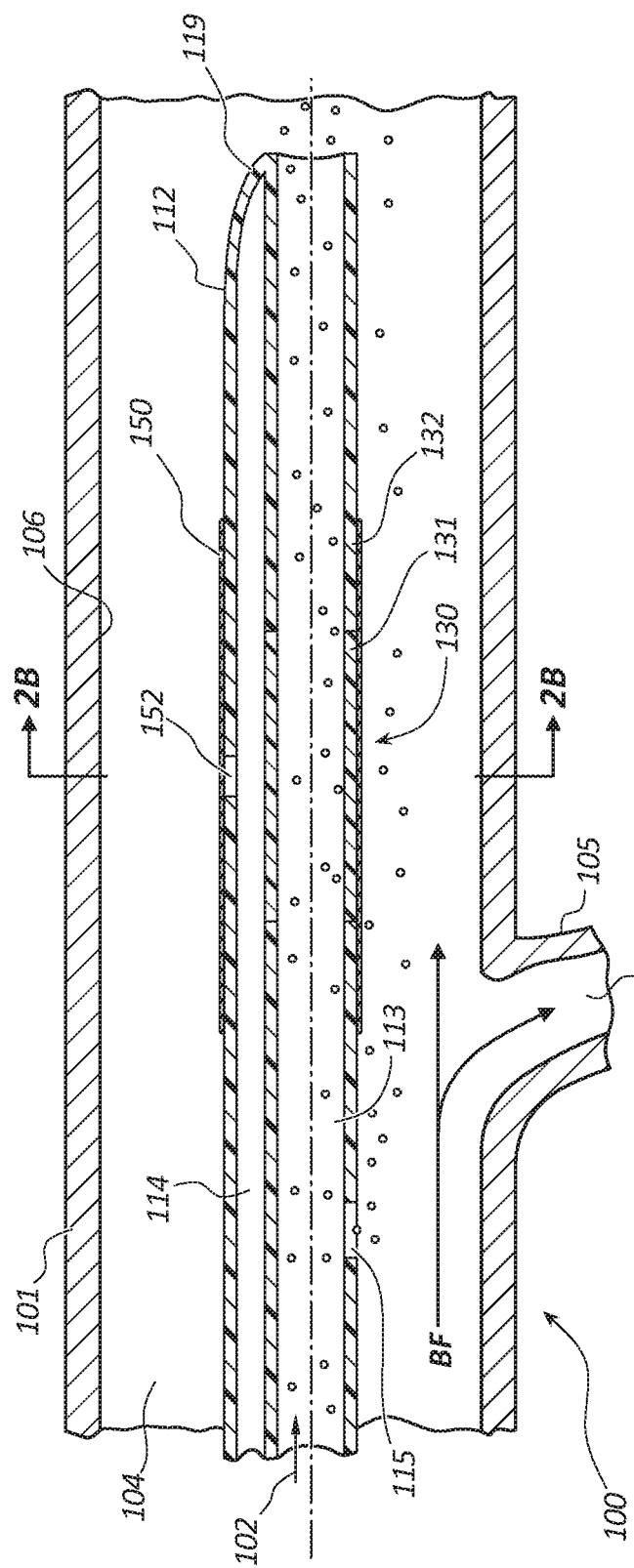
FIG. 2A is a side cross-sectional view of a distal portion of the embolization catheter of FIG. 1 in a non-occlusion state, the embolization catheter disposed within a vessel.
Figure 2B:
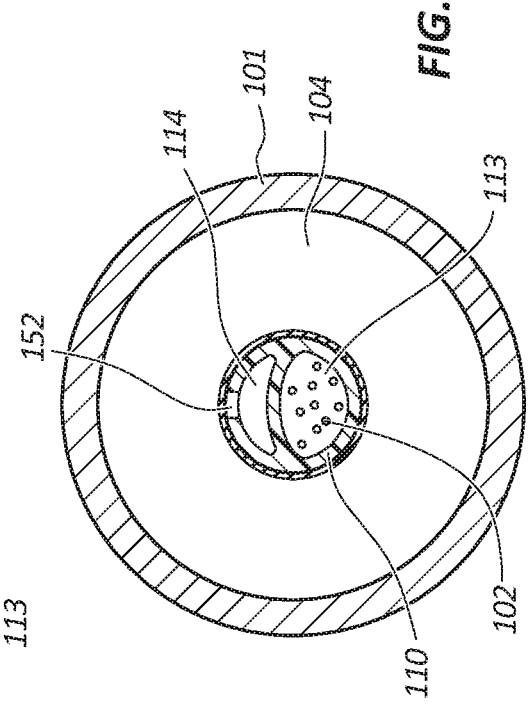
FIG. 2B is a transverse cross-sectional view, taken through plane 2B-2B of FIG. 2A, of a distal portion of the embolization catheter in the non-occlusion state, the embolization catheter disposed within a vessel.

In the illustrated embodiment, the flow restriction member 130 is disposed at the distal end 112 of the body 110. As depicted in the illustrated embodiment, the flow restriction member 130 may include a compliant segment 131 of the guidewire lumen 113. In the illustrated embodiment, the compliant segment 131 comprises a wall 132 formed from a compliant material, such as polyurethane, silicone rubber, thermoplastic elastomer, etc. The compliant segment 131 may be configured to collapse inwardly when the expandable member 150 is expanded as shown in FIGS. 3A-3B. When collapsed, the compliant segment 131 may restrict flow of liquids and/or embolic materials 102 out the distal end 112 of the body 110 and diverts the flow through the proximal port 115. Thus, in the depicted embodiment, the flow restriction member 130 may be understood as selectively actuated to direct flow of fluid and/or embolic materials 102 out the proximal port 115. In other words, the flow of fluid and/or embolic materials 102 is out the distal end 112 of the body 110 when the flow restriction member 130 is not actuated (such as shown in FIGS. 2A-2B) and is out the proximal port 115 when the flow restriction member 130 is actuated by expansion of the expandable member 150 (such as shown in FIGS. 3A-3B). When in an actuated state, as shown in FIGS. 3A-3B, the flow restriction member 130 may include a distal portion and a proximal portion that are funnel shaped. A closed passage 133 may extend between the distal and proximal portions. The closed passage 133 may be openable by a guidewire (such as a guidewire inserted into the guidewire lumen 113) while the flow restriction member 130 is in the actuated state, while sealing around the guidewire. The funnel shape of the distal and proximal portions facilitates front loading and back loading of the guidewire into the body guidewire lumen 113. Further, the closed passage 133 may be configured to seal around a guidewire this is disposed within the guidewire lumen 113 as the flow restriction member 130 is actuated.

In another embodiment, the flow restriction member 130 may be configured in a permanently closed or actuated state. In this embodiment, the flow restriction member 130 may be a preformed member disposed within the guidewire lumen 113, such as a silicone member coupled to an inside diameter of the guidewire lumen 113 in a shape similar to the shape of the flow restriction member 130 when in the actuated state as shown in FIG. 3A. The flow restriction member 130 may include distal and proximal portions that are funnel shaped. In such embodiments, the closed passage 133 may be traversable or otherwise openable by a guidewire inserted through, or extending from the distal portion to the proximal portion while maintaining a seal around the guidewire.

In the illustrated embodiment, the handle portion 140 is coupled to the proximal end 111 of the body 110. As illustrated, the handle portion 140 includes a guidewire port 141 and a pressurization port 142. The guidewire port 141 is in fluid communication with the guidewire lumen 113. The guidewire port 141 may be configured to facilitate passage of a guidewire into and out of the guidewire lumen 113. The guidewire port 141 may also be configured to couple with a fluid and/or embolic material delivery device to deliver the fluid and/or embolic material 102 into the guidewire lumen 113. The pressurization port 142 is in fluid communication with the pressurization lumen 114. The pressurization port 142 may be configured to couple with a pressurization device (e.g., syringe) that contains air or fluid (e.g., saline). The pressurization port 142 may direct passage of the air or fluid from the pressurization device into the pressurization lumen 114 to expand the expandable member 150.

In some embodiments, the embolization catheter 100 may be used to deliver an embolic material to a vessel in order to occlude blood flow to a tumor or lesion. The embolization catheter 100 may be used, for example, in a trans-arterial embolization (TAE) procedure where an embolic material is injected into a vessel to occlude the vessel. The embolic material may comprise polyvinyl alcohol, hydrogel, gelatin, microspheres, etc. The embolization catheter 100 may also be used in a trans-arterial chemoembolization (TACE) procedure where an embolic material that includes a chemotherapy drug is injected into a vessel to occlude the vessel and deliver a chemotherapy drug to a tumor or lesion. The embolization catheter 100 may additionally be used in a trans-arterial radioembolization (TARE) procedure where an embolic material that includes a radioactive isotope (e.g., yttrium-90) is injected into a vessel to occlude the vessel and deliver small amounts of radiation to a tumor or lesion. The embolization catheter 100 may be used in procedures to deliver embolic materials to vessels of the liver, prostrate, brain, kidney, bladder, etc.

In use, as depicted in FIGS. 2A-3B, the embolization catheter 100 may be inserted over a guidewire into the vessel 101 that has blood flow into a tumor or lesion. The expandable member 150 may be positioned distal of a branch vessel 105 of the vessel 101. In the configuration shown in FIGS. 2A-2B, the flow restriction member 130 is in a non-actuated state. When utilized in this state, embolic material 102 may be delivered into the guidewire lumen 113 such that the embolic material 102 flows out of the guidewire lumen 113 at the distal end 112 of the body 110 into the blood flowing within the vessel 101. The embolic material 102 may flow distally to occlude the vessel 101 at a location distal of the embolization catheter 100 and adjacent the tumor or lesion to cause tumor or lesion cell death. In some instances, the embolic material 102 may also flow proximally due to turbulence within the vessel 101 and enter the branch vessel 105 causing occlusion of the vessel branch 105, which may or may not be a desirable clinical outcome, depending on the target of the procedure.

FIGS. 3A-3B depict the expandable member 150 expanded and the flow restriction member 130 in the actuated state. Air or fluid may be delivered to the expandable member 150 to cause the expandable member 150 to expand. When expanded, an outer surface of the expandable member 150 may contact and seal against the vessel wall 106 to prevent blood from flowing (blood flow BF direction indicated by arrow) distally of the embolization catheter 100. The expanded expandable member 150 may also center the distal end 112 of the body 110 within the vessel lumen 104. Expansion of the expandable member 150 may also cause actuation of the flow restriction member 130 to occlude the guidewire lumen 113. When the embolic material 102 is delivered into the guidewire lumen 113, with the embolization catheter 100 in this state, the embolic material 102 may thus be restricted from flowing out of the guidewire lumen 113 at the distal end 112 of the body 110 by the actuated or closed flow restriction member 130. Flow of the embolic material 102 may be directed through the proximal port 115, into the vessel lumen 104, and into the branch vessel 105 to occlude the branch vessel 105 while preventing flow of the embolic material 102 into other vessels. The guidewire lumen 113 may be flushed with a liquid (e.g., saline) to displace the embolic material 102 from the guidewire lumen 113 and vessel lumen 104 and into the branch vessel 105. In such procedures, the branch vessel 105 may be targeted for delivery of embolic material if the branch vessel 105 provides a blood supply to a tumor or lesion targeted for treatment.

FIGS. 4A-4B depict an embodiment of an embolization catheter 200 that resembles the embolization catheter 100 described above in certain respects. Accordingly, like features are designated with like reference numerals, with the leading digit incremented to "2." For example, the embodiment depicted in FIGS. 4A-4B includes a flow restriction member 230 that may, in some respects, resemble the flow restriction member 130 of FIGS. 1-3A. Relevant disclosure set forth above regarding similarly identified features thus may not be repeated hereafter. Moreover, specific features of the embolization catheter 100 and related components shown in FIGS. 1-3B may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the embolization catheter 200 and related components depicted in FIGS. 4A-4B. Any suitable combination of the features, and variations of the same, described with respect to the embolization catheter 100 and related components illustrated in FIGS. 1-3B can be employed with the embolization catheter 200 and related components of FIGS.

4A-4B, and vice versa. This pattern of disclosure applies equally to further embodiments depicted in subsequent figures and described hereafter, wherein the leading digits may be further incremented.

FIGS. 4A-4B illustrate a distal portion of an embolization catheter 200. The illustrated embodiment can include a body 210, the flow restriction member 230, and an expandable member 250. As depicted, the body 210 includes an embolic material delivery or guidewire lumen 213 and a pressurization lumen 214. The guidewire lumen 213 is co-axially disposed within the pressurization lumen 214. The lumens 213, 214 may be sized analogously to the lumens described in connection with the embodiment of FIGS. 1-3B. In the embodiment of FIGS. 4A-4B, the expandable member 250 is coupled to the body 210 adjacent to a distal end 212 of the body 210. A pressurization port 252 provides fluid communication between the pressurization lumen 214 and an interior volume of the expandable member 250. The body 210 includes a proximal port 215 that is disposed proximal of the expandable member 250. The proximal port 215 provides fluid communication between the guidewire lumen 213 and a vessel lumen 204. The proximal port 215 may be sized, shaped, or otherwise configured analogous to the port discussed in connection with the embodiment of FIGS. 1-3B. Noting the coaxial arrangement of the guidewire lumen 213 and pressurization lumen 214, the proximal port 215 may be configured to prevent fluid communication between the pressurization lumen 214 and the vessel lumen 204, while allowing communication between the vessel lumen 204 and the guidewire lumen 213.

In the embodiment of FIGS. 4A-4B, the flow restriction member 230 may be disposed at the distal end 212 of the body 210. The flow restriction member 230 may be configured as a one-way or check valve. Examples of suitable one-way or check valve types include duckbill, flapper, slit, etc. The illustrated embodiment depicts a duckbill valve 235. The duckbill valve 235 may be disposed over the distal end 212 of the body 210 such that the guidewire lumen 213 and the pressurization lumen 214 are blocked. The duckbill valve 235 may provide an atraumatic tip configuration configured to engage with a vessel wall 206 without causing damage. An outer sleeve 237 of the duckbill valve 235 may circumferentially surround and may be fixedly coupled to the distal end 212. A duckbill portion 236 may be disposed within the guidewire lumen 213 and directed proximally. In this orientation, a higher pressure within the guidewire lumen 213 than within the vessel lumen 204 causes the duckbill portion 236 to seal and a lower pressure within the guidewire lumen 213 than within the vessel lumen 204 causes the duckbill portion 236 to open. Additionally, this orientation may be configured to facilitate passage of a guidewire as the embolization catheter 200 is advanced over a guidewire.

FIGS. 4A-4B depict a distal portion of the embolization catheter 200 disposed within the vessel lumen 204 such that the expandable member 250 is positioned distally of a branch vessel 205. As depicted, the expandable member 250 is in an expanded state. Air or fluid may be delivered to the expandable member 250 to cause the expandable member 250 to expand. When expanded, an outer surface of the expandable member 250 may contact and seal against the vessel wall 206 to prevent blood from flowing (blood flow BF direction indicated by arrow) distally of the embolization catheter 200. The expanded expandable member 250 may also center the distal end 212 or the body 210 within the vessel lumen 204. An embolic material 202 may be delivered into the guidewire lumen 213 and prevented from flowing out of the distal end 212 by the flow restriction member 230. Flow of the embolic material 202 may be directed through the proximal port 215, into the vessel lumen 204, and into the branch vessel 205 to occlude the branch vessel 205 while limiting or preventing flow of the embolic material 202 into other vessels distal of the embolization catheter 200. The guidewire lumen 213 may be flushed with a liquid (e.g., saline) to displace the embolic material 202 from the guidewire lumen 213 and vessel lumen 204 and into the branch vessel 205.

FIGS. 5A-5C depict another embodiment of an embolization catheter 300. The depicted embodiment may include a body 310, a flow restriction member 330, an expandable member 350, and a handle 340. The flow restriction member 330 may be similar to flow restriction members previously described. The body 310 of the illustrated embodiment includes a guidewire tube 321 and a pressurization tube 322. In other embodiments, the body 310 may include three, four, five, or more tubes. The guidewire tube 321 and the pressurization tube 322 are longitudinally coupled together such that the tubes 321, 322 extend longitudinally parallel to each other. A junction 345 is disposed at a proximal end 311 of the tubes 321, 322. A guidewire lumen extension tube 343 is coupled to the junction 345 and extends proximally from the junction 345. The guidewire lumen extension tube 343 can be in fluid communication with a guidewire lumen 313. A pressurization lumen extension tube 344 is coupled to the junction 345 and extends proximally from the junction 345. The pressurization lumen extension tube 344 can be in fluid communication with a pressurization lumen 314. A guidewire port 341 may be coupled to a proximal end of the guidewire lumen extension tube 343. A pressurization port 342 may be coupled to a proximal end of the pressurization lumen extension tube 344.

The expandable member 350 is disposed adjacent a distal end 312 of the body 310. The expandable member 350 may be coupled to the pressurization tube 322 and in fluid communication with the pressurization lumen 314. As illustrated in FIG. 5B, the expandable member 350 may include a first balloon 351 and a second balloon 352. When expanded, the balloons 351, 352 may be configured to surround the guidewire tube 321 and the pressurization tube 322 and to occlude a vessel lumen. In another embodiment, as shown in FIG. 5C, the expandable member 350 may include a single balloon 355 comprising a first lobe 353 and a second lobe 354. The balloon 355 may be configured to surround the guidewire tube 321 and the pressurization tube 322 and to occlude the vessel lumen. Embodiments with additional balloons and balloons with other shapes configured to collectively occlude a vessel lumen during a procedure are also within the scope of this disclosure.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially perpendicular" is recited with respect to a feature, it is understood that in further embodiments, the feature can have a precisely perpendicular configuration.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. An embolization catheter, comprising:
    an elongate body, comprising:
        a first lumen;
        a second lumen; and
        a proximal port in fluid communication with the first lumen;
    an expandable member in fluid communication with the second lumen; and
    a flow restriction member configured to occlude a distal portion of the first lumen,
    wherein the flow restriction member is disposed distal of the proximal port,
    wherein the proximal port is disposed proximal of the expandable member such that the proximal port is in communication with blood flow from a proximal direction when the expandable member is expanded, and
    wherein embolic material passes out of the elongate body through the proximal port when the flow restriction member occludes the first lumen.

2. The embolization catheter of claim 1, wherein the expandable member is a balloon.

3. The embolization catheter of claim 1, wherein the flow restriction member is a one-way valve.

4. The embolization catheter of claim 1, wherein the flow restriction member is configured to be selectively closed.

5. The embolization catheter of claim 4, wherein the flow restriction member is closed by pressure from the expandable member when the expandable member is expanded.

6. The embolization catheter of claim 1, wherein the expandable member is configured to occlude a vessel.

7. An embolization catheter system, comprising:
    an embolization catheter comprising:
        an elongate body, comprising a first lumen and a second lumen;
        an expandable member;
        a valve member configured to occlude the first lumen; and
        a proximal port disposed proximal of the expandable member; wherein the proximal port is in fluid communication with the first lumen;
    an embolic material; and
    a guidewire,
    wherein the valve member is configured to receive the guidewire,
    wherein the elongate body is configured to direct flow of the embolic material through the first lumen, and
    wherein the proximal port is in communication with blood flow from a proximal direction when the expandable member is expanded.

8. The embolization catheter system of claim 7, wherein the valve member is disposed distally of the proximal port.

9. The embolization catheter system of claim 7, wherein the valve member is a one-way valve.

10. The embolization catheter system of claim 7, wherein the valve member is configured to be selectively closed.

11. The embolization catheter system of claim 10, wherein the valve member is closed by pressure from the expandable member when the expandable member is expanded.

12. The embolization catheter system of claim 7, wherein the expandable member is configured to occlude a vessel.

13. A method of embolizing a vessel, comprising: obtaining an embolization catheter comprising:
    an elongate body, comprising a first lumen and a second lumen;
    an expandable member;
    a valve member configured to occlude the first lumen; and
    a proximal port in fluid communication with the first lumen,
    wherein the proximal port is disposed proximal of the expandable member such that the proximal port is in communication with blood flow from a proximal direction when the expandable member is expanded;
    wherein the valve member is disposed distal of the proximal port;
inserting the embolization catheter into the vessel;
expanding the expandable member; and
dispensing embolic material out of the elongate body through the proximal port.

14. The method of claim 13, further comprising occluding the first lumen distal of the proximal port.

* * * * *